United States Patent [19]

Lal et al.

[11] 4,400,506

[45] Aug. 23, 1983

[54] PROCESSES FOR THE MANUFACTURE OF PYRIMIDO[6,1-A]ISOQUINOLINONES

[75] Inventors: Bansi Lal; Adolf D'Sa; Horst Dornauer; Noel J. de Souza, all of Bombay, India

[73] Assignee: Hoechst Aktiengesellschaft, Frankfurt am Main, Fed. Rep. of Germany

[21] Appl. No.: 314,994

[22] Filed: Oct. 26, 1981

Related U.S. Application Data

[63] Continuation of Ser. No. 201,796, Oct. 29, 1980, abandoned, which is a continuation of Ser. No. 90,129, Nov. 1, 1979, abandoned.

[30] Foreign Application Priority Data

Nov. 3, 1978 [DE] Fed. Rep. of Germany ....... 2847693

[51] Int. Cl.³ ................. C07D 471/04; A61K 31/505
[52] U.S. Cl. .................................... 544/246; 544/244; 544/252; 424/251
[58] Field of Search ................. 544/252, 244, 246; 424/251

[56] References Cited

U.S. PATENT DOCUMENTS

| | | | |
|---|---|---|---|
| 3,021,351 | 2/1962 | Lombardino et al. | 544/252 |
| 3,081,306 | 3/1963 | Lombardino et al. | 544/252 |
| 3,476,755 | 11/1969 | Taylor et al. | 424/251 X |
| 3,594,379 | 7/1971 | Hardtmann et al. | 424/251 X |
| 3,609,152 | 9/1971 | Hess et al. | 424/251 X |
| 3,876,788 | 4/1975 | Hodson et al. | 424/251 |

FOREIGN PATENT DOCUMENTS

| | | |
|---|---|---|
| 862785 | 7/1978 | Belgium . |
| 10759 | 5/1980 | European Pat. Off. ............ 424/251 |
| 2720085 | 11/1978 | Fed. Rep. of Germany . |
| 2801289 | 5/1979 | Fed. Rep. of Germany . |
| 2847693 | 5/1980 | Fed. Rep. of Germany . |
| 147624 | 5/1980 | India . |
| 46-09467 | 3/1971 | Japan .................. 544/252 |
| 77/06706 | 11/1977 | South Africa . |

OTHER PUBLICATIONS

Kaneko, et al., Chemical Abstracts, vol. 71, 61326y (1969).
Nair, et al., Chemical Abstracts, vol. 71, 101682v (1969).
Kaneko, et al., Chemical Abstracts, vol. 75, 36106b (1971).
Lal, et al., Chemical Abstracts, vol. 95, 73469f (1981).
Hoechst Pharmaceuticals Ltd., Chemical Abstracts, vol. 97, 144868q (1982).
Popp, et al., Chemical Reviews, vol. 58, pp. 321–401 (1958) p. 331.
Yamasaki, et al., J. Pharm. Soc. (Japan) vol. 82, pp. 352–355 (1962).
Chemical Abstracts 78, 111360x (1973).
Chemical Abstracts 83, 43266x (1975).
Chemical Abstracts 94, 84152c (1981).
Atta-ur-Rahman et al., Tet. Letters No. 47, 4101–4102 (1977).
Atta-ur-Rahman, JCS Perkin I, 736–738 (1972).
Kutney et al., J. Am. Chem. Soc. 92, 1727–1735 (1970).
Wenkert et al., Canad. J. Chem. 42, 489–490 (1964).
Kobor, Chem. Abstr. 87, 84789w (1977).
Capuano et al., Chem. Ber. 108, 1541–1547 (1975).

Primary Examiner—Donald G. Daus
Assistant Examiner—Diana G. Rivers
Attorney, Agent, or Firm—Curtis, Morris & Safford

[57] ABSTRACT

What are disclosed are compounds of the formula

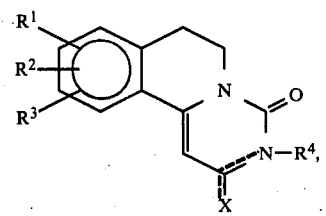

wherein, X is oxygen, sulfur, or halogen, useful as intermediates in the preparation of certain pyrimido(6,1-a)isoquinolin-4-ones having pharmaceutical utilities, and methods for making said intermediates.

5 Claims, No Drawings

PROCESSES FOR THE MANUFACTURE OF PYRIMIDO[6,1-A]ISOQUINOLINONES

This is a continuation of application Ser. No. 201,796, filed Oct. 19, 1980 and now abandoned, which is in turn a continuation of Ser. No. 90,129, filed Nov. 1, 1979 and now abandoned.

This invention relates to pyrimido(6,1-a)isoquinolin-4-one derivatives, to new intermediates used in their preparation and to novel processes for the preparation of the pyrimido(6,1-a)isoquinolin-4-ones of the invention.

More particularly, the present invention relates to pyrimido(6,1-a)isoquinolin-4-ones of the formula I,

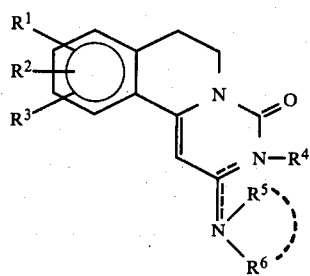

in which $R^1$, $R^2$ and $R^3$, which may be the same or different, stand for hydrogen, hydroxy, $C_1$-$C_6$-alkoxy, or halogen, two of the radicals $R^1$, $R^2$ or $R^3$ when in adjacent positions and taken together, may form a methylenedioxy or an ethylenedioxy group, $R^4$ stands for hydrogen, $C_1$-$C_6$-alkyl, $C_3$-$C_6$-cycloalkyl, alkyl having up to 6 carbon atoms, which may substituted by $C_1$-$C_3$-alkoxy, di($C_1$-$C_4$-alkyl)amino or di($C_1$-$C_4$-alkyl)phosphin($C_1$-$C_4$)alkyl, aralkyl having up to 8 carbon atoms, in which the aryl radical may be mono- or polysubstituted by halogen, nitro, $C_1$-$C_3$-alkoxy and/or $C_1$-$C_3$-alkyl, heterocyclic alkyl or aryl which may be mono- or polysubstituted by halogen, $C_1$-$C_3$-alkyl, $C_1$-$C_3$-alkoxy, halo-$C_1$-$C_3$-alkyl, amino, hydroxy or the group —OMet, wherein Met is an alkali metal atom, or $R^4$ stands for an electron pair, if $R^5$ stands for one of the following radicals, $R^5$ and $R^6$, which may be the same or different, stand for hydrogen, hydroxy, $C_{1-6}$-alkoxy, amino, $C_{1-3}$-alkylamino, di-$C_{1-3}$-alkylamino, arylamino, amino which may be substituted by a five or six-membered carbon ring having up to 3 hetero atoms selected from N,O or S or stand for $C_{1-6}$-alkyl, $C_{3-7}$-cycloalkyl, hydroxy-$C_{1-6}$-alkyl, alkoxy-$C_{1-6}$-alkyl, dialkoxy-$C_{1-6}$-alkyl, halo-$C_{1-6}$-alkyl, di-$C_{1-4}$-alkylamino-$C_{1-6}$-alkyl, $C_{6-8}$-aralkyl, $C_{1-6}$-acyl and aryl which may be substituted and which stands for an automatic hydrocarbon radical having up to 10 carbon atoms, or $R^5$ stands for an electron pair, if $R^4$ stands for one of the above radicals and $R^5$ and $R^6$, when taken together with the nitrogen atom to which they are bound, stand for a nitrogen heterocycle, which may be substituted and which may contain a further nitrogen or oxygen atom.

The present invention relates further to pyrimido(6,1-a)isoquinolin-4-ones of the formula II

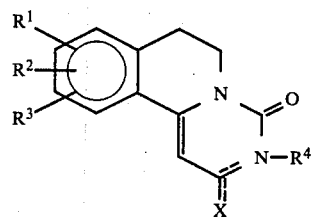

wherein $R^1$, $R^2$ and $R^3$ are as defined in formula I and $R^4$, in case

X is oxygen or sulfur, represents the substituents defined in formula I or, in case X is a halogen atom, stands for an electron pair.

The compounds of the formula II are used as intermediates in the preparation of the compounds of the formula I.

If at least one of the radicals $R^5$ and $R^6$ stands for hydrogen, there are also included in the above definition of the pyrimido(6,1-a)isoquinolin-4-one derivatives of the formula I the isomers Ib corresponding to the following formula and which may be obtained by complete isomerization of the compounds of the formula Ia or which are in equilibrium with the compounds of the formula Ia.

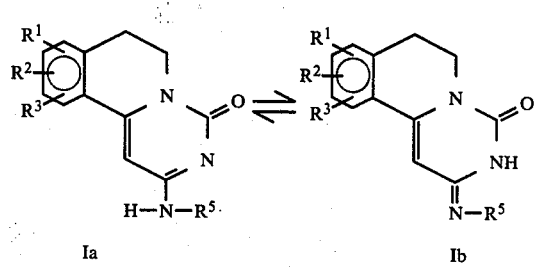

There is also included in the definition of the pyrimido(6,1-a)isoquinolin-4-one derivatives the Ic-isomer of the following formula Ic

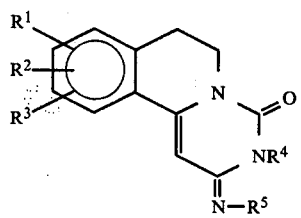

wherein $R^1$, $R^2$, $R^3$, $R^4$ and $R^5$ are as defined above.

If $R^1$, $R^2$, $R^3$ stand for $C^1$-$C^6$-alkoxy groups, those having up to 3 carbon atoms are preferred.

If $R^1$, $R^2$ or $R^3$ stand for halogen, chlorine is preferred.

As alkyl radicals for $R^4$, preferably methyl, ethyl, n-propyl, isopropyl, butyl, isobutyl, sec-butyl or tert-butyl are used.

Examples of aralkyl radicals for $R^4$ are those having at most 8 carbon atoms, in which the aryl radical may be substituted one, two or three times, preferably one time, by substitutents such as halogen, nitro, $C_1$-$C_3$-alkoxy, and $C_1$-$C_3$-alkyl.

Suitable heterocyclic alkyl radicals for $R^4$ are, for example, furfuryl and tetrahydrofurfuryl.

Suitable examples of aryl radicals for $R^4$ are phenyl radicals optionally substituted one or several times, preferably one, two or three times, by halogen, for example fluorine, chlorine and bromine, $C_1$-$C_3$-alkyl and $C_1$-$C_3$-alkoxy, for example methyl, ethyl, methoxy and ethoxy, haloalkyl, for example trifluoromethyl, or by amino or hydroxy, in the latter the hydrogen atoms possibly being replaced by an alkali metal, for example sodium.

Suitable nitrogen-containing heterocyclic radicals for $R^4$ are, for example, pyrrolidino, piperidino, morpholino, and piperazino, optionally substituted by $C_1$-$C_3$-alkyl, $C_2$-$C_4$-alkoxycarbonyl, optionally substituted phenyl or a nitrogen heterocycle.

Suitable alkylamino or dialkylamino radicals for $R^5$ or $R^6$ are in particular those having alkyl groups with at most 3 carbon atoms, for example methylamino or dimethylamino.

Suitable arylamino radicals for $R^5$ or $R^6$ are phenylamino, the phenyl moiety of which may be substituted one or several times by halogen, for example chlorine, by alkyl having at most 3 carbon atoms, for example methyl, or by the nitro group. A suitable amino group substituted by a nitrogen-containing heterocycle, for $R^5$ or $R^6$, is, for example N-morpholinoamino.

As alkyl radicals for $R^5$ or $R^6$, there may be mentioned those having at most 6 carbon atoms, for example methyl, ethyl, n-propyl, isopropyl, butyl, isobutyl, sec.-butyl or tert.butyl.

Suitable cycloalkyl radicals for $R^5$ or $R^6$ are those having at most 6 carbon atoms, for example cyclohexyl.

Suitable substituted alkyl radicals for $R^5$ or $R^6$ are those having up to 6 carbon atoms, which may be substituted by one or two hydroxy or alkoxy groups each of the latter having at most 3 carbon atoms, or by halogen, for example chlorine, or by amino or dialkylamino, the alkyl groups of which having at most 4 carbon atoms, further dialkylphosphinylalkyl, for example dimethylphosphinylmethyl.

Examples of aralkyl radicals for $R^5$ or $R^6$ are those having at most 8 carbon atoms, wherein the aryl moiety may be substituted one or several times, especially one, two or three times, by any of the substitutents as specified above for $R^1$.

Suitable heterocyclic alkyl radicals for $R^5$ or $R^6$ are, for example, furfuryl or tetrahydrofurfuryl.

Suitable aryl radicals for $R^5$ or $R^6$ are, for example phenyl, which may be substituted one or several times, especially one, two or three times, by halogen atoms, for example fluorine, chlorine or bromine, by alkyl or alkoxy groups having at most 3 carbon atoms, for example methyl, ethyl, methoxy and ethoxy, by haloalkyl groups, for example trifluoromethyl, or by amino or hydroxy, the hydrogen atoms in the hydroxy groups being optionally replaced by an alkali metal, for example sodium.

Examples of suitable radicals of nitrogen-containing heterocycles include pyrrolidino, piperidino, morpholino or piperazino, which may be substituted by alkyl, alkoxycarbonyl, aryl or a nitrogen heterocycle, with alkyl, alkoxy, aryl or the nitrogen heterocycle having the above meaning.

Examples of suitable acyl radicals for $R^5$ or $R^6$ are straight chain or branched alkanoyl radicals having from 1 to 6 carbon atoms such as acetyl or aroyl, such as benzoyl, the phenyl moiety being optionally substituted one or several times by the substituents specified above for $R^5$ and $R^6$, provided that these latter stand for aryl.

Suitable salts of the pyrimido(6,1-a)isoquinolin-4-one derivatives of the formula I are, for example, those of inorganic or organic acids, for example hydrochlorides, hydrobromides, sulfates, phosphates, acetates, oxalates, tartrates, citrates, maleates or fumarates.

Suitable quaternary ammonium salts of the pyrimido(6,1-a)isoquinolin-4-one derivatives of the formula I are, for example those derived from alkylhalides such as methyliodides.

The preferred substituents are:

$C_{1-3}$-alkoxy for $R^1$ and $R^2$, hydrogen for $R^3$; $C_{1-6}$-alkyl or phenyl which may be substituted one or three times by one of the above substitutents for $R^5$; hydrogen for $R^6$ and hydrogen for $R^4$ in case of X being oxygen or an electron pair for $R^4$ in case of X being chlorine.

Particularly preferred compounds of the formula I are:

9,10-Dimethoxy-2-tert.butylamino-6,7-dihydro-4H-pyrimido(6,1-a)isoquinolin-4-one hydrochloride,
9,10-dimethoxy-2-sec.butylamino-6,7-dihydro-4H-pyrimido(6,1-a)isoquinolin-4-one hydrochloride,
9,10-dimethoxy-2-(2,6-dimethylanilino)-6,7-dihydro-4H-pyrimido(6,1-a)isoquinolin-4-one,
9,10-dimethoxy-2-(2,4-dimethylanilino)-6,7-dihydro-4H-pyrimido(6,1-a)isoquinolin-4-one,
9,10-dimethoxy-2-(2-chloroanilino)-6,7-dihydro-4H-pyrimido(6,1-a)isoquinolin-4-one hydrochloride monohydrate and
9,10-dimethoxy-2-(2,4,6-trimethylanilino)-6,7-dihydro-4H-pyrimido(6,1-a)isoquinolin-4-one hydrochloride dihydrate.

Particularly preferred compounds of the formula II are:

9,10-Dimethoxy-3,4,6,7-tetrahydro-<u>2H</u>-pyrimido(6,1-a)isoquinolin-2,4-dione.
2-Chloro-9,10-dimethoxy-6,7-dihydro-<u>4H</u>-pyrimido(6,1-a)isoquinolin-4-one.
2-Chloro-9,10-methylenedioxy-6,7-dihydro-<u>4H</u>-pyrimido(6,1-a)isoquinolin-4-one.

In the following Table I, there are listed some of the pyrimido(6,1-a)isoquinolin-4-one derivatives of the formula II.

TABLE I

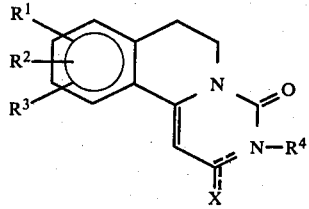

II

| $R^1$ | $R^2$ | $R^3$ | $R^4$ | X | Melting Point (°C.) |
|---|---|---|---|---|---|
| H | H | H | H | O | 308-309 |
| 9-OCH₃ | 10-OCH₃ | H | H | O | 323-325 |
|  | 10-Cl | H | — | O | 250 |
| H | H | H | — | Cl | 179-180 |
| 9-OCH₃ | 10-OCH³ | H | — | Cl | 235-236 |
| H | 10-Cl | H | — | Cl | 250 |
| 9,10(—OCH₂O—) |  | H | — | Cl | 245-247 |

It is another object of the invention to provide novel barbituric acid derivatives of the formula III, suitable for the preparation of the pyrimido(6,1-a)isoquinolin-4-ones of formula II.

In particular, there are disclosed below two novel barbituric acid derivatives, viz. 1-(3,4-dimethoxyphenethyl)barbituric acid and 1-(3,4-methylendioxyphenethyl)barbituric acid, with their respective melting points.

TABLE II

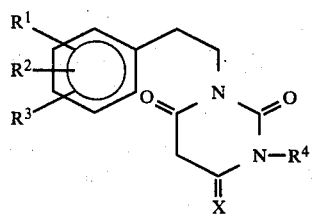

III

| $R^1$ | $R^2$ | $R^3$ | $R^4$ | X | Melting Point (°C.) |
|---|---|---|---|---|---|
| 3-OCH$_3$ | 4(OCH$_3$)$_2$ | | H | O | 185–187 |
| 3,4-(—OCH$_2$O—) | | | H | O | 222–224 |

The present invention further relates to a process for preparing the compounds of the aforesaid formula I, which comprises (a) subjecting a barbituric acid derivative of the formula III

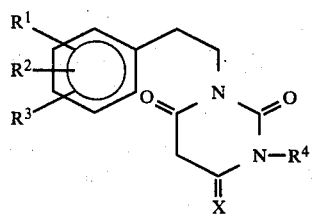

III wherein $R^1$, $R^2$, $R^3$ and $R^4$ are as defined in formula I and X stands for oxygen and sulfur, to a cyclization reaction in the presence of a dehydrating agent, for example in the presence of an acid such as polyphosphoric acid, phosphorus pentoxide, or sulfuric acid, to yield a compound of the formula II, wherein $R^1$, $R^2$, $R^3$, $R^4$ and X are as defined above, or in the presence of an acid halide such as phosphorus oxychloride, thionyl chloride or an appropriate inorganic halide such as phosphorus pentachloride, to yield a compound of the formula II, wherein $R^1$, $R^2$, $R^3$ and $R^4$ are as defined in formula I and X stands for a halogen atom, in particular chlorine, and (b) reacting the resulting compound of the formula II with a compound of the formula

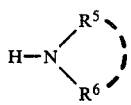

wherein $R^5$ and $R^6$ are as defined in formula I, in the presence of a base, whereupon the product can converted with an acid to the salt, in the form of the free base.

In the case when the reaction is carried through with an acid like polyphosphoric acid, the reaction may be accelerated or completed by the application of heat, for example by heating to 80°–150°. In the cases when the reactions are carried out with an acid halide or an inorganic halide, the reactions may be carried out in the presence of a solvent, such as ethers, for example dioxane and tetrahydrofuran, aliphatic halogenated hydrocarbons, for example chloroform, or aromatic hydrocarbons, for example benzene and toluene. The reaction may be accelerated by heating to the boiling point of the solvent.

The base used in process step (b) may be the compound of the formula

itself which may be used in excess, calculated on the quantity needed for the reaction, or an alkali metal hydride, for example sodium hydride, or a tertiary amine, for example triethylamine, or an acid scavenger, for example, diazabicyclononene. The reaction may be carried out in the presence of polar solvents, for example dimethylformamide, dimethyl sulfoxide, aliphatic halogenated hydrocarbons, for example chloroform, or alkanols, for example butanol, or in the presence of aprotic solvents, for example high-boiling ethers such as diethylene glycol dimethyl ether. The reaction may be accelerated by the application of heat, for example by heating to the boiling point of the solvent.

The compounds of the formula I, wherein $R^5$ or $R^6$ stand for an acyl radical, are obtainable from compounds of the formula I, wherein at least one of the radicals $R^5$ or $R^6$ stands for hydrogen, by treating the latter compounds with an acyl halide or an acyl anhydride, the acyl group being alkanoyl having at most 6 carbon atoms, for example acetyl, or aroyl, for example benzoyl with the phenyl nucleus being optionally substituted as specified above, and the halide moiety of the acyl halide being optionally chlorine, for example. The reaction may be carried out in the presence of a base such as alkali metal carbonate, for example potassium carbonate, or of a tertiary amine, for example triethylamine. The reaction may be accelerated by heating to the boiling point of the acylating agent.

The barbituric acid derivatives of the formula III used as intermediates are obtainable by methods known in the literature. When, for example, $R^4$ stands for hydrogen and X stands for oxygen, the following reaction sequence may be adopted

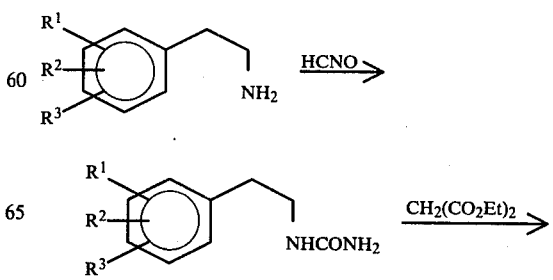

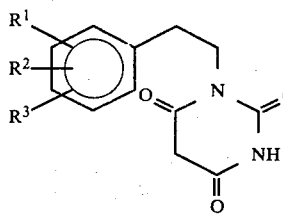

according to the procedures as described for the formation of urea by C. F. Kurzer in Organic Synthesis, Coll. Vol. 4 (1963) and of barbituric acids by J. B. Dickey and A. R. Gray in Organic Synthesis, Coll. Vol. 2 (1943).

The pyrimido(6,1-a)isoquinoline-4-one derivatives according to the formula I are distinguished by valuable pharmacological properties, for example, a hypotensive, broncho-dilatory and anti-allergic activity.

Because of their hypotensive activity, the novel active substances are suitable for the prophylaxis and treatment of cardio-vascular diseases, for example essential and malignant hypotony, myovascular insufficiency, angina pectoris and disturbances of the peripheric circulatory system. The active substances may also be used in combination with other pharmacologically active substances, for example diuretics, antiarhythmic agents, β-blockers, tranquilizers, agents with cardiovascular dilatory activity, hypolipidemics etc.

Because of their broncho-dilatory and anti-allergic activity, the novel active substance are suitable for the prophylaxis and treatment of diseases of the respiratory system, for example bronchial asthma, chronic bronchitis, emphysema, and allergic reactions, for example allergic asthma, hay fever, allergic rhinitis, conjunctivitis, urticaria etc. The active substance may also be used in combination with other pharmacologically active substances, for example corticosteroids, sympathomimetics, xanthine derivatives, antihistaminics, tranquilizers, cardiac stimulants etc.

The active substantives according to the invention can be administered perorally, parenterally (intramuscularly, intraveneously, subcutaneously), rectally, as an aerosol or topically.

The following examples illustrate the invention:

EXAMPLE 1

9,10-Dimethoxy-3,4,6,7-tetrahydro-2H-pyrimido(6,1-a)isoquinolin-2,4-dione (formula II)

Polyphosphoric acid (10.0 g) is heated to 105° C. and and 1.0 g of 1-(3,4-dimethoxyphenylethyl)barbituric acid is added with mechanical stirring. The reaction mixture is heated for 4 hours and poured onto crushed ice to give a white solid. The solid is filtered, washed with water, dried and crystallized from dimethylformamide.

Yield: 500 mg. M.p. 323°–325° C.

EXAMPLE 2

2-Chloro-9,10-dimethoxy-6,7-dihydro-4H-pyrimido(6,1-a)isoquinolin-4-one (formula II)

A mixture of 1-(3,4-dimethoxyphenylethyl)barbituric acid (20.2 g) and phosphorus oxychloride (100 ml) is refluxed for 2.5 hours at 100°–110° C. The excess of phosphorus oxychloride is distilled. The residue is poured onto crushed ice and made basic with a cold solution of 30% aqueous sodium hydroxide. A yellow gummy precipitate is separated and extracted with chloroform. The extract is washed with water, dried over sodium sulfate and concentrated to dryness under reduced pressure. The residue is purified by passage over a silica gel column using chloroform as eluent to give the desired compound.

Yield: 20.2 g (ca. 100%), m.p. 235°–236° C.

EXAMPLE 3

2-Chloro-8,10-methylenedioxy-6,7-dihydro-4H-pyrimido(6,1-a)isoquinolin-2-one (formula II)

The procedure described in Example 2 is followed by using 1-(3,4-methylenedioxyphenylethyl)barbituric acid instead of 1-(3,4-dimethoxyphenylethyl)barbituric acid.

Yield: 80%. M.p. 245°–247° C.

EXAMPLE 4

9,10-Dimethoxy-3-methyl-3,4,5,7-tetrahydro-4H-pyrimido(6,1-a)isoquinolin-2,4-dione (formula II)

A mixture of 9,10 dimethoxy-3,4,6,7-tetrahydro-2H-pyrimido(6,1-a)isoquinolin-2,4-dione (4.11 g), oil-free sodium hydride (0.75 g) and dimethyl formamide (100 ml) is heated for 15 minutes to 100° C. and subsequently cooled to room temperature. Methyl iodide (10 ml) is added thereto. The reaction mixture is heated for 12 hours at 100° C. The solvent is removed in vacuo and the residue is treated with cold water. The solid is filtered and recrystallized from acetic ester-methylene chloride.

Yield: 4.0 g. M.p. 260°–262° C.

EXAMPLE 5

9,10-Dimethoxy-2-tert.butylamino-6,7-dihydro-4H-pyrimido(6,1-a)isoquinolin-4-one hydrochloride (formula I)

A solution of 9,10-dimethoxy-2-chloro-6,7-dihydro-4H-pyrimido(6,1-a)isoquinolin-4-one (3.0 g) and tert.-butylamine (10.0 ml) in chloroform (75.0 ml) is refluxed for 16 hours. The solvent is evaporated under reduced pressure and the residue is triturated with a dilute solution of sodium hydroxide to give a white precipitate. The precipitate is filtered, dried, dissolved in ethanol and converted to its hydrochloride by treating it with hydrochloric acid. The hydrochloride is crystallized from an ethanol-ether mixture.

Yield: 3.0 g. M.p. 265°–270° C.

What is claimed is:

1. The method of making a compound of the formula

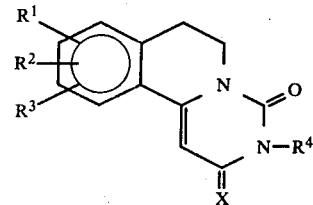

wherein $R^1$, $R^2$, and $R^3$, taken alone, are the same or different and are hydrogen, hydroxy, $C_1$–$C_6$-alkoxy, or halogen, or any two of $R^1$, $R^2$, and $R^3$, when in adjacent positions and taken together, are methylenedioxy or ethylenedioxy; X is oxygen or sulfur; and $R^4$ is hydrogen, $C_1$–$C_6$-alkoxy, $C_3$–$C_6$-cycloalkyl, $C_1$–$C_6$-alkyl substituted by $C_1$–$C_3$-alkoxy, by di($C_1$–$C_4$-alkyl)amino, or by di($C_1$–$C_4$-alkyl)phosphin($C_1$–$C_4$)alkyl, aralkyl having up to 8 carbon atoms or such aralkyl wherein the aryl group is mono- or poly-substituted by at least one member selected from the group consisting of halogen, nitro, $C_1-C_3$-alkoxy, and $C_1-C_3$-alkyl, heterocyclic alkyl or aryl or such heterocyclic alkyl or aryl mono- or poly-substituted by halogen, $C_1-C_3$-alkyl, $C_1-C_3$-alkoxy, halo-$C_1-C_3$-alkyl, amino, hydroxy, or by the group —OMet wherein Met is an alkali metal atom, which method comprises cyclizing a barbituric acid compound of the formula

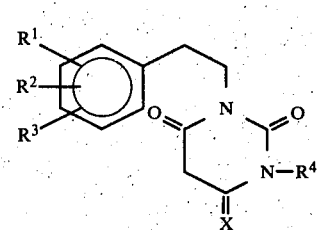

wherein X is oxygen or sulfur, in the presence of an acid.

2. A method as in claim 1 wherein $R^4$ is hydrogen and wherein the compound made by the method is subsequently reacted with a compound of the formula $R^4Z$, wherein $R^4$ is other than hydrogen and Z is halogen.

3. A method as in claim 1 wherein said barbituric acid compound is cyclized in the presence of polyphosphoric acid at a temperature from 80° C. to 150° C.

4. The method of making a compound of the formula

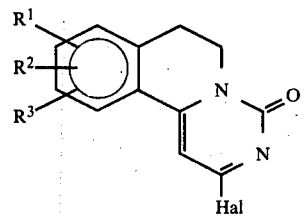

wherein $R^1$, $R^2$, and $R^3$, taken alone, are the same or different and are hydrogen, hydroxy, $C_1-C_6$-alkoxy, or halogen, or any two of $R^1$, $R^2$, and $R^3$, when in adjacent positions and taken together, are methylenedioxy, and Hal is halogen, which method comprises cyclizing a barbituric acid compound of the formula

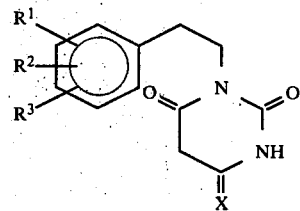

wherein X is oxygen or sulfur, in the presence of an inorganic acid halide or of a phosphorus pentahalide.

5. A method as in claim 4 wherein said barbituric acid compound is cyclized in the presence of phosphorus oxychloride, phosphorus pentachloride, or thionyl chloride in the presence of a solvent.

* * * * *